(12) United States Patent
Kasprzak et al.

(10) Patent No.: US 9,522,073 B2
(45) Date of Patent: Dec. 20, 2016

(54) ORIENTATION MARKERS FOR ENDOVASCULAR DELIVERY SYSTEM

(71) Applicant: Cook Medical Technologies LLC, Bloomington, IN (US)

(72) Inventors: Piotr Miroslaw Kasprzak, Regensburg (DE); Werner Ducke, Eight Mile Plains (AU); Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/761,442

(22) Filed: Feb. 7, 2013

(65) Prior Publication Data

US 2013/0204342 A1 Aug. 8, 2013

(30) Foreign Application Priority Data

Feb. 8, 2012 (AU) ................... 2012200735

(51) Int. Cl.
*A61F 2/95* (2013.01)
*A61F 2/07* (2013.01)
(Continued)

(52) U.S. Cl.
CPC . *A61F 2/95* (2013.01); *A61F 2/07* (2013.01); *A61F 2/954* (2013.01); *A61F 2/962* (2013.01);
(Continued)

(58) Field of Classification Search
CPC ............ A61F 2/95; A61F 2/962; A61F 2/954; A61F 2/07; A61F 2002/9511; A61F 2002/061; A61F 2250/0097
(Continued)

(56) References Cited

U.S. PATENT DOCUMENTS

| 5,383,852 A | 1/1995 | Stevens-Wright |
| 5,429,617 A | 7/1995 | Hammersmark et al. |

(Continued)

FOREIGN PATENT DOCUMENTS

| WO | 2010127040 A1 | 11/2010 |
| WO | 2011116308 A1 | 9/2011 |

OTHER PUBLICATIONS

International Search Report and Written Opinion for PCT/US2011/029037, dated Jul. 21, 2011, 10 pages.

(Continued)

*Primary Examiner* — Ryan J Severson
*Assistant Examiner* — Anh Dang
(74) *Attorney, Agent, or Firm* — Brinks Gilson & Lione

(57) ABSTRACT

An endovascular stent graft delivery device has portion to remain outside a patient in use and a proximal portion to be introduced into a patient. The proximal portion has a dilator at the proximal end and a length extending module is fastened to the dilator and extends proximally. The length extending module has a proximal end which in use extends out of the patient. The dilator has a dilator marker and the length extending module has a first and second marker at the distal and proximal ends of the length extending module. The first marker and the second marker are at the same relative circumferential position on the length extending module so that the rotational position of the elongate body within the patient can be determined.

20 Claims, 6 Drawing Sheets

(51) Int. Cl.
*A61F 2/954* (2013.01)
*A61F 2/962* (2013.01)
*A61F 2/06* (2013.01)

(52) U.S. Cl.
CPC .. *A61F 2002/061* (2013.01); *A61F 2002/9511* (2013.01); *A61F 2250/0097* (2013.01)

(58) Field of Classification Search
USPC .............. 623/1.11, 1.12, 1.35; 606/108, 200
See application file for complete search history.

(56) References Cited

U.S. PATENT DOCUMENTS

| | | | |
|---|---|---|---|
| 5,746,766 | A | 5/1998 | Edoga |
| 5,921,978 | A | 7/1999 | Thompson et al. |
| 6,285,903 | B1 | 9/2001 | Rosenthal et al. |
| 6,520,934 | B1 | 2/2003 | Lee et al. |
| 6,695,875 | B2 | 2/2004 | Stelter et al. |
| 6,827,726 | B2 | 12/2004 | Parodi |
| 6,849,087 | B1 | 2/2005 | Chuter |
| 7,108,715 | B2 | 9/2006 | Lawrence Brown et al. |
| 7,344,556 | B2 | 3/2008 | Seguin et al. |
| 7,393,357 | B2 | 7/2008 | Stelter et al. |
| 7,815,608 | B2 | 10/2010 | Schafersman et al. |
| 7,867,270 | B2 | 1/2011 | Hartley et al. |
| 7,930,014 | B2 | 4/2011 | Huennekens et al. |
| 7,998,186 | B2 | 8/2011 | Hartley |
| 8,012,193 | B2 | 9/2011 | Hartley et al. |
| 8,014,849 | B2 | 9/2011 | Peckham |
| 8,043,354 | B2 | 10/2011 | Greenberg et al. |
| 8,118,854 | B2 | 2/2012 | Bowe |
| 8,262,718 | B2 | 9/2012 | Chuter |
| 2004/0006381 | A1 | 1/2004 | Sequin et al. |
| 2005/0059890 | A1* | 3/2005 | Deal et al. ............... 600/433 |
| 2005/0113686 | A1 | 5/2005 | Peckham |
| 2005/0159773 | A1 | 7/2005 | Broome et al. |
| 2005/0255317 | A1 | 11/2005 | Bavaro et al. |
| 2006/0241465 | A1 | 10/2006 | Huennekens et al. |
| 2007/0083215 | A1 | 4/2007 | Hamer et al. |
| 2007/0123910 | A1 | 5/2007 | Hartley et al. |
| 2007/0250154 | A1 | 10/2007 | Greenberg et al. |
| 2008/0221656 | A1* | 9/2008 | Hartley et al. ............... 623/1.11 |
| 2011/0270375 | A1 | 11/2011 | Hartley et al. |
| 2011/0270376 | A1 | 11/2011 | Hartley |
| 2011/0295111 | A1 | 12/2011 | Hansis et al. |
| 2012/0172968 | A1 | 7/2012 | Chuter et al. |
| 2013/0030514 | A1 | 1/2013 | Kasprzak et al. |

OTHER PUBLICATIONS

International Preliminary Report on Patentability for PCT/US2011/029037, dated Mar. 22, 2012, 6 pages.
Response to International Search Report and Written Opinion, dated Jan. 19, 2012, 11 pages.
International Patent Examination Report No. 1 for Australian Patent Application No. 2012200735 dated Jun. 20, 2012, 8 pages.
Office Action/Restriction received in related U.S. Appl. No. 13/635,573 dated May 2, 2013, 7 pages.
Response to Office Action/Restriction filed in related U.S. Appl. No. 13/635,573 dated May 9, 2013, 12 pages.
Office Action received in related U.S. Appl. No. 13/635,573 dated Aug. 6, 2013, 13 pages.
Response to Office Action filed in related U.S. Appl. No. 13/635,573 dated Aug. 15, 2013, 14 pages.
Notice of Allowance received in related U.S. Appl. No. 13/635,573 dated Oct. 29, 2013, 11 pages.

* cited by examiner

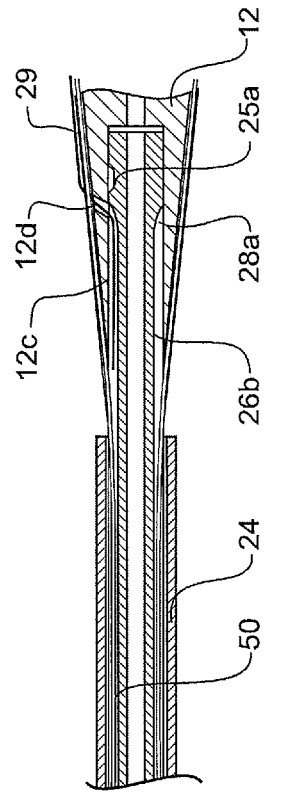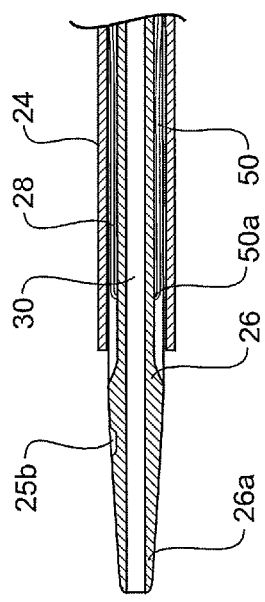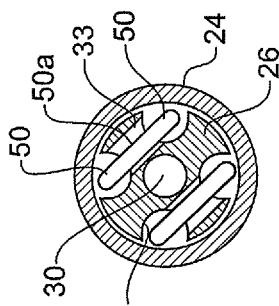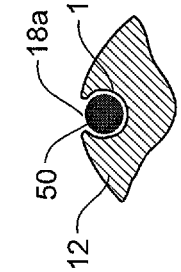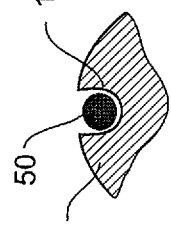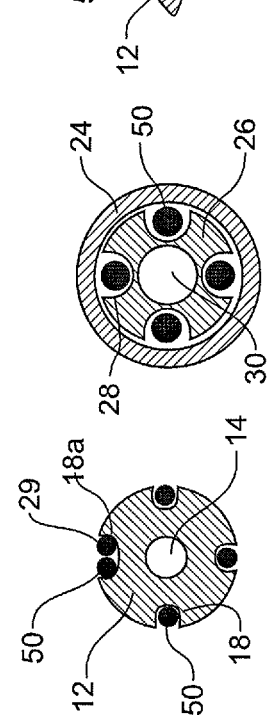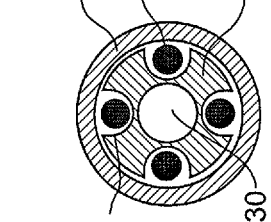

ORIENTATION MARKERS FOR ENDOVASCULAR DELIVERY SYSTEM

FIELD OF INVENTION

This invention relates to a medical device and more particularly to a medical device for the facilitation endovascular delivery of medical devices.

BACKGROUND

This invention will be discussed in particular in relation to the delivery and cannulation of thoracoabdominal stent grafts but the invention is not so limited.

Thoracoabdominal aneurysms are particularly difficult to treat due to the inclusion of four branch vessels (celiac artery, superior mesenteric artery, and renal arteries). Endovascular devices are available which include four branches, but cannulation of each branch independently can be difficult and time consuming, exposing the patient to large amount of contrast and x-rays.

Preloaded wires associated with a fenestrated stent graft and a delivery device have been demonstrated to greatly ease the process of cannulating the branches of the device. In the case of a thoracoabdominal aneurysm, a fenestrated or side arm stent graft with four preloaded wires with catheters or sheaths are required for the four side branches or fenestrations. Since a preloaded delivery system including four lumens for four catheters or preloaded sheaths in the delivery device would be unacceptably large (28 Fr), an alternative option is to individually cannulate the branches using preloaded guide wires from a brachial access site. To accomplish this, the preloaded wires must be inserted from the femoral access with a main delivery device and tracked through the abdominal and thoracic aorta, and out through the brachial artery.

PCT Patent Application Number PCT/US2011/029037 (published as WO 2011/116308) entitled "INTRODUCER WITH EXTENSION" lodged on 18 Mar. 2011 discloses devices and arrangements for delivery of fenestrated or branched stent grafts using delivery devices incorporating preloaded guide wires and the teaching therein is incorporated herein in its entirety.

The assembly of an endovascular delivery device incorporating indwelling guide wires requires that there be some way of ensuring that a manufacturer places the correct indwelling wire into the correct side arm and then that a physician using the device will know which indwelling guide wire passes through which side arm. During introduction and placement a delivery device is often rotated to encourage it to pass trough the vasculature and it may in fact remain partially twisted. Some method is needed to ensure that a physician knows the actual orientation of the endovascular device so that the physician knows which indwelling wire is which when most of the device is hidden within the human or animal body.

It is to overcome some of these problems that the present invention is directed or to alt least provide the practitioner with a useful alternative.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

BRIEF DESCRIPTION OF THE INVENTION

In one form the invention comprises an endovascular stent graft delivery device comprising an elongate body and a length extending module, the elongate body comprising a distal portion to remain outside a patient in use and a proximal portion to be introduced into the body to carry a stent graft to a placement site, the proximal portion comprising a nose cone dilator at the proximal end thereof and the length extending module being releasably fastened to the nose cone dilator and extending proximally of the nose cone dilator, the length extending module comprising a distal end which is releasably fastened to the nose cone dilator and a proximal end which in use extends out of the patient, the nose cone dilator comprising a dilator marker and the length extending module comprising a first marker and a second marker, the first marker being at the distal end of the length extending module and the second marker being at the proximal end of the length extending module, the first marker and the second marker being at the same relative circumferential position on the length extending module and the length extending module is releasably fastened to the nose cone dilator with the first marker and the dilator marker rotationally aligned whereby the rotational position of the elongate body within the patient can be determined by the observation of the position of the second marker.

In a preferred embodiment the dilator marker comprises an aperture in the nose cone dilator and the first marker and the second marker each comprise a recess in the length extending module. Other forms of visual marking such as colour patches are also within the scope of the invention.

In use during assembly the length extending module is releasably joined to the nose cone dilator with the dilator marker aligned circumferentially with the first marker. In a preferred embodiment the first marker, the second marker and the dilator marker are all placed so that in use they are all at a 12 o'clock position with respect to vasculature of a patient, the 12 o'clock position being defined by the anterior position of the vasculature.

Preferably the endovascular stent graft delivery device comprises a plurality of indwelling guide wires extending from the distal portion of the elongate body, through the stent graft to the dilator and through the length extending module, whereby the endovascular stent graft delivery device can be introduced into a patient via a femoral artery and the length extending module can extend out an artery of the thoracic arch whereby to extend the indwelling guide wires out of the artery of the thoracic arch.

Preferably the length extending module comprises an elongate extension sheath and an extension dilator in the extension sheath and the extension dilator extending distally and proximally of the extension sheath, the extension dilator comprising a plurality of longitudinal grooves on an outside surface thereof and the plurality of indwelling guide wires extending along respective longitudinal grooves.

A stent graft is carried on the proximal portion of the elongate body, the stent graft comprising a tubular body, the tubular body comprising proximal and distal open ends and a plurality of fenestrations or side arms, each of the indwelling guide wires extending through a respective fenestration or side arm, the indwelling guide wires extending through the tubular body proximally of the respective fenestration or side arm and outside the tubular body distally of the respective fenestration or side arm.

Preferably the nose cone dilator at the proximal end of the elongate body comprises a plurality of longitudinal grooves on an outside surface thereof to receive respective indwelling guide wires therealong.

Preferably the plurality of longitudinal grooves on at least a part of the outside surface of the dilator comprise a substantially closed tube except for a narrow elongated opening whereby the respective indwelling guide wires are received and retained therein.

Preferably the dilator comprises a proximal aperture and the length extending module is removably engaged into the proximal aperture.

Preferably the length extending module is removably engaged with the dilator by a trigger wire release mechanism, whereby upon release of the trigger wire release mechanism the length extending module can be removed from the dilator.

Preferably the plurality of indwelling guide wires comprise a first and a second continuous indwelling guide wire, each continuous wire extending from the distal portion of the elongate body to the proximal end of the length extending module and returning to the distal portion of the elongate body.

Preferably the length extending module comprises a pair of cross apertures extending into the extension dilator between adjacent longitudinal grooves at the proximal end of the extension dilator whereby each of the first and second indwelling guide wires pass through a respective cross aperture to return in an adjacent longitudinal groove.

In an alternative form the invention comprises a length extending module for an endovascular delivery device, the length extending module being able to be releasably fastened to a dilator of the endovascular delivery device and arranged to extend proximally of the dilator in use, the length extending module comprising a distal end which is able to be releasably fastened to the dilator and a proximal end which is use extends out of a patient, the length extending module comprising a first marker and a second marker, the first marker being at the distal end of the length extending module and the second marker being at the proximal end of the length extending module, the first marker and the second marker being at the same relative circumferential position whereby the orientation or rotational position of the endovascular delivery device within the patient can be determined by the observation of the position of the second marker.

BRIEF DESCRIPTION OF THE DRAWINGS

This then generally describes the invention but to assist with understanding reference will now be made to the accompanying drawings which show preferred embodiments of the invention and a process for use of the device of the present invention.

In the drawings

FIG. 4 shows a longitudinal cross section in detail of a portion of the delivery device shown in FIG. 1 in an assembled condition;

FIG. 5A to 5E show a transverse cross sectional views of portions of the stent graft delivery device according to the present invention;

DESCRIPTION OF PREFERRED EMBODIMENTS

Figure 1:
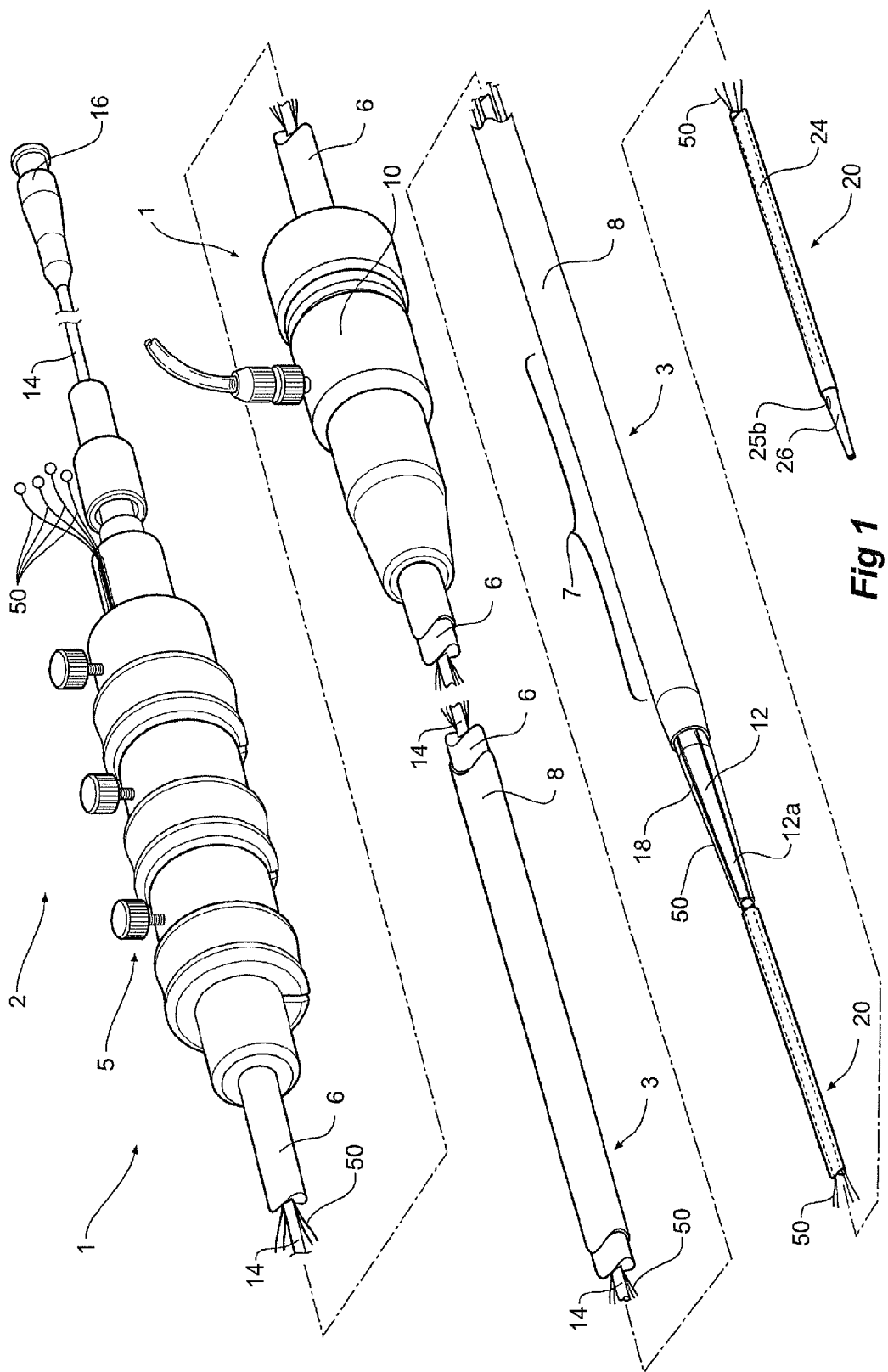
FIG. 1 shows a stent graft delivery advice according to one embodiment of the present invention.

Now looking at the drawings in more detail and in particular FIG. 1 in which a stent graft deployment device of one embodiment of the present invention is shown.

FIG. 1 shows the stent graft delivery device in a condition for introduction into a patient. The delivery device 1 comprises a handle portion 2 and an introduction portion 3. The handle portion is intended to remain outside a patient in use and the introduction portion is intended to be introduced into a patient via a puncture into an artery such as the femoral artery. A pusher catheter 6 extends proximally from a trigger wire release region 5 of the handle 2. A sheath 8 and sheath hub 10 extends over the pusher catheter 6. The sheath 8 extends proximally to a nose cone dilator 12. The sheath can be retracted to expose a stent graft retained below it. The stent graft is retained on the delivery device in the region distally of the nose cone dilator 12 indicated by the reference numeral 7. A guide wire cannula 14 extends from a Luer lock hub 16 at the distal end of the device through the handle and pusher catheter to extend to and through the nose cone dilator 12. The Luer lock hub 16 is used to introduce liquids such as contrast media to enable tracking of the progress of an operation.

The nose cone dilator 12 has a plurality of longitudinal grooves 18 on its outside longitudinal surface. The grooves are shown in detail in FIGS. 2, 3 and 4. Into these grooves 18 lie indwelling guide wires 50 as will be discussed below in more detail.

A length extending module 20 is releasably mounted to the proximal end 12a of the nose cone dilator 12 as discussed in more detail below.

The stent graft is retained in a compressed condition under the sheath 8 just distal of the node cone dilator by releasable trigger wires (not shown) and when the sheath is withdrawn the stent graft expands. In this configuration the proximal end of the stent 40 continues to be retained to the introducer device at a point just distal of the nose cone dilator 12 until it is ultimately released by removal of the releasable trigger wires. U.S. Pat. No. 7,803,177 entitled Trigger Wire System issued Sep. 28, 2010 shows trigger wire systems suitable for retaining stent grafts onto delivery devices and the teachings therein a incorporated herein in their entirety.

Figure 2:
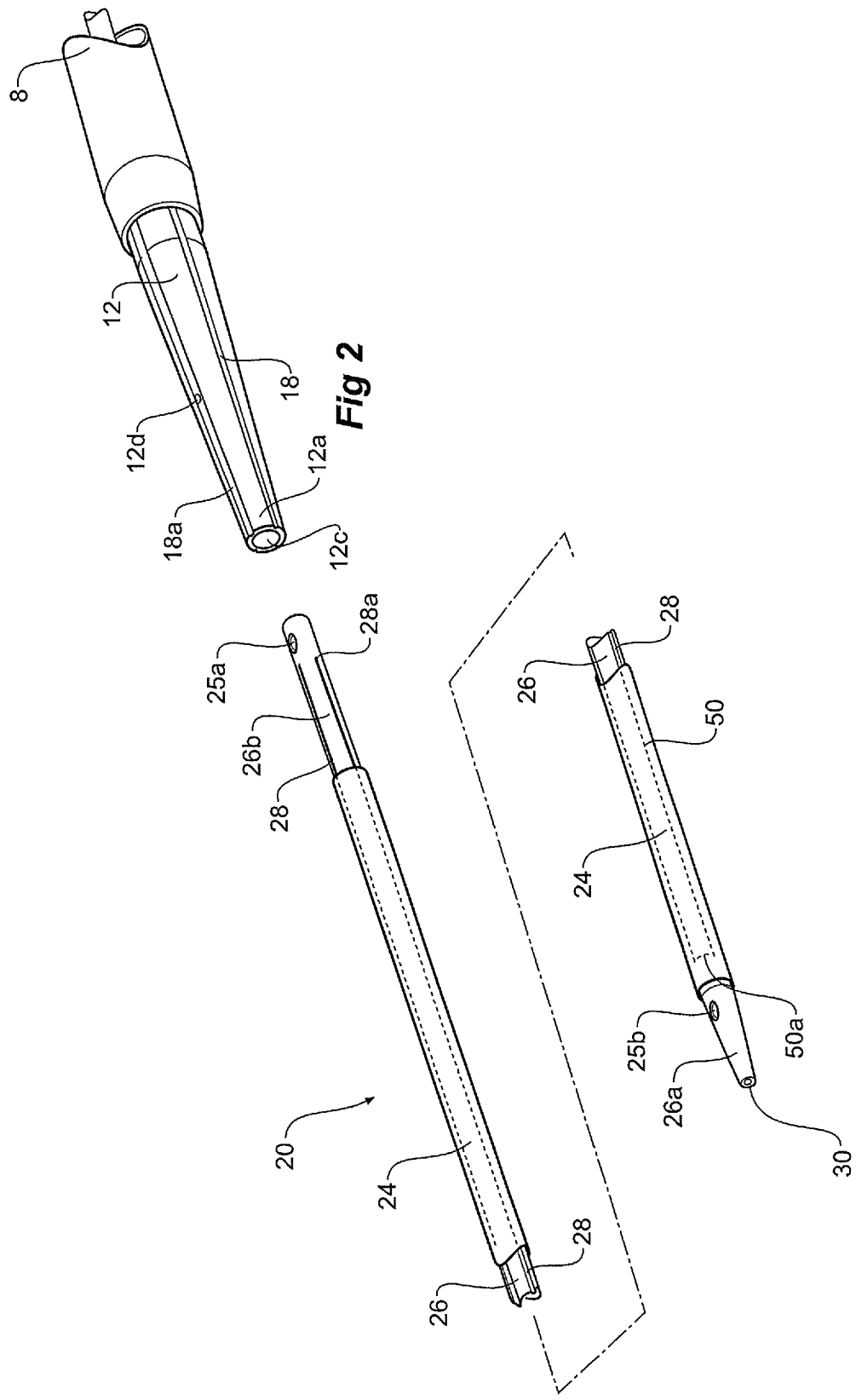
FIG. 2 shows detail of a portion of the delivery device shown in FIG. 1 in a part assembled condition.
Figure 3:
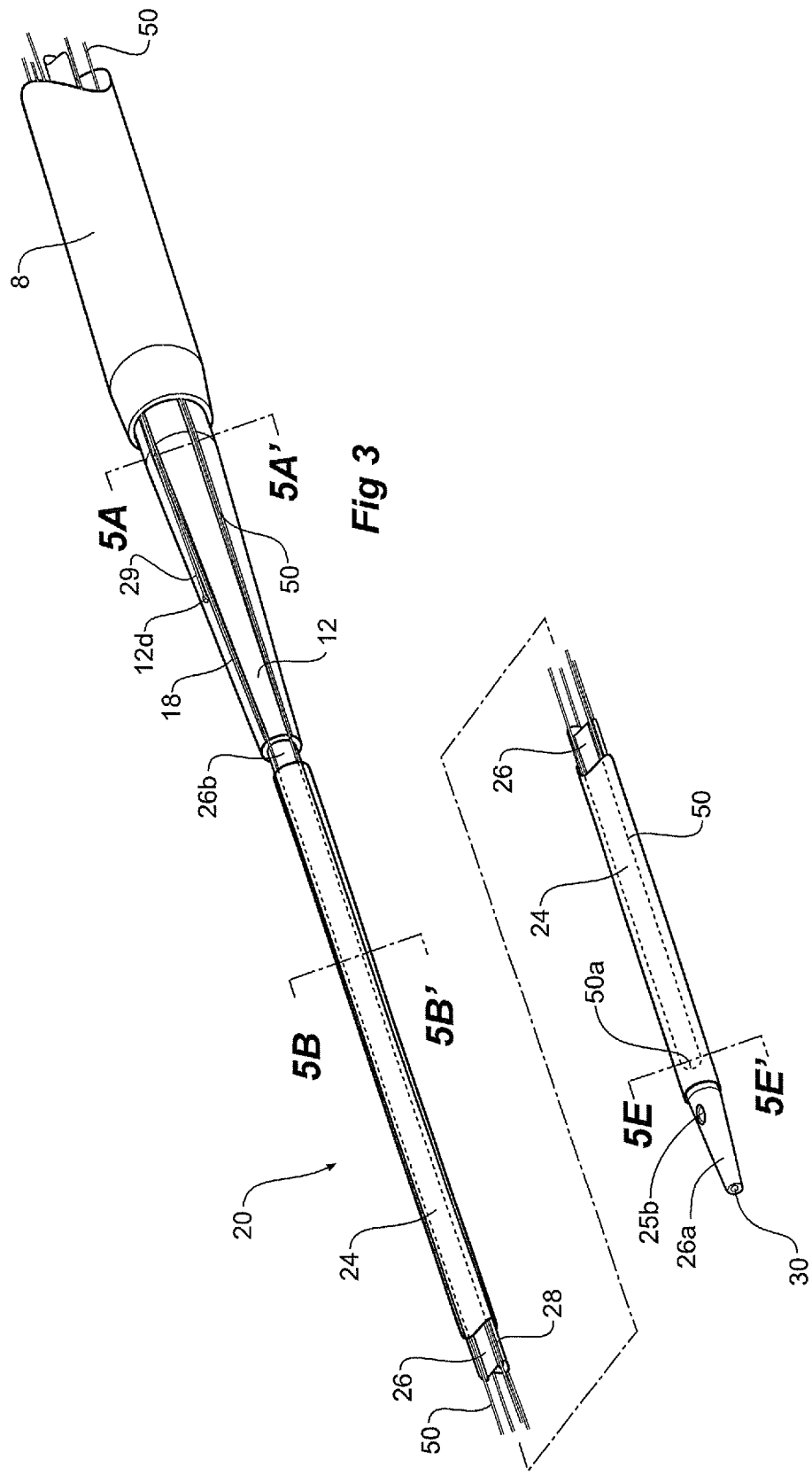
FIG. 3 shows detail of a portion of the delivery device shown in FIG. 1 in an assembled condition.

FIGS. 2 and 3 show detail of a proximal portion of the delivery device incorporating the length extending module of the present invention shown in FIG. 1 in a part assembled and an assembled condition, respectively. The indwelling guide wires are omitted in FIG. 2 to assist with clarity although normally they would be present at this stage of assembly.

The length extending module 20 comprises a flexible extension dilator 26 surrounded by a flexible sheath 24. The extension dilator 26 extends proximally of the sheath to a dilator tip 26a and distally of the sheath at a dilator distal end 26b.

The extension dilator 26 of the length extending module 20 has a plurality of longitudinal groves 28 on its outside surface. Into these grooves 28 lie the indwelling guide wires 50 as shown in FIG. 3. The indwelling guide wires 50 are retained in the grooves 28 by the sheath 24. The dilator 26 also has a guide wire lumen 30. The longitudinal grooves 28 terminate at 28a before the distal end 26b of the dilator 26 and also terminate before the dilator tip 26a at the proximal end of the extension dilator.

FIG. 5A shows a cross section along the line 5A-5A' on the tapered region nose cone dilator 12 of FIG. 3. The tapered region of the nose cone dilator 12 has four longitudinal grooves 18 arranged orthogonally on its outer surface. Into each of these grooves is received an indwelling guide wire 50. A detail of such a groove is shown in FIG. 5C. Also shown in FIG. 5A is the trigger wire 29. The groove 18a is wider than the other grooves 18 so that the trigger wire 29 and the indwelling guide wire 50 can both be received into the groove. This ensures, particularly in the region of the nose cone dilator which is engaged by the sheath 8 (see FIG. 3) that the overall diameter of the device is not increased.

As an alternative, the grooves 18 in the nose come dilator may be as shown in FIG. 5D. In this embodiment the grooves 18 are a substantially closed tube except for a narrow elongated opening 18a whereby the respective indwelling guide wires are received and retained therein. Preferably the substantially closed portion of the grooves 18 is on the tapered portion of the nose cone dilator. With the indwelling guide wires retained in the substantially closed groove there is less chance of the wire coming out of the groove during deployment and possible causing trouble entangling with other portions of the delivery device. The nose cone dilator is formed from a polyurethane vinyl material which exhibits a degree of elasticity or flexibility so that when it is desired to remove the indwelling guide wire the sides of the opening can be deflected to allow removal. During use of the delivery device of the present invention as discussed in more detail below a sheath and dilator are fed down over the indwelling guide wire from the proximal end and the dilator acts to draw the indwelling guide wire out of the substantially closed groove.

FIG. 5B shows a transverse cross section of the length extending module. In this embodiment it will be seen that there are four grooves 28 in the outer surface of the extension dilator 26 into which the indwelling guide wires 50 are received to extend from the distal end of the extension dilator 26b to the proximal end 26a. A central aperture 30 is for traversing the length extending module over a guide wire as discussed below.

FIG. 5E shows a transverse cross sectional view of a proximal end of the length extending module 20. The extension dilator 26 has four longitudinal grooves 28 into each of which is received an indwelling guide wire 50. At the proximal end 26a of the extension dilator 26 two cross apertures 33 are cut into the extension dilator to join two pairs of adjacent longitudinal apertures 28 so that the indwelling wire 50 can cross over at 50a to extend back down the adjacent longitudinal groove 28. By this arrangement there are no free ends of the indwelling guide wires at the proximal end and once they have been exposed at the shoulder of a patient as discussed below the cross over part 50a of the wire 50 can be cut to give individual guide wires. The indwelling guide wires are used for pre-catheterisation of side arms of the stent graft.

The dilator distal end 26b has a first marker 25a and the dilator tip 26a has a second marker 25b. Both of the markers 25a and 25b are at the same relative circumferential position on the length extending module 20. Hence, knowing where the marker is at one end of the length extending module enables a physician, in use, to know where the other end is. This can be useful because during a medical procedure the delivery device is twisted and rotated to encourage it to pass through the vasculature of a patient and at times is passed through some convoluted vasculature and there may be part twists remaining in the delivery device so that it is not immediately apparent which indwelling guide wire is which.

The length extending module 20 is releasably mounted to the proximal end 12a of the nose cone dilator 12 by the dilator distal end 26b being received into a forwardly facing dilator recess 12c in the nose cone dilator. The nose cone dilator 12 has a side aperture 12d which extends into the forwardly facing dilator recess 12c within the dilator. The aperture 12d receives a trigger wire as is explained below with reference to FIG. 4 for selective retention and release of the length extending module from the delivery device. The aperture 12d is placed on the nose cone dilator 12 at a selected circumferential position and is the dilator marker.

FIG. 2 shows the length extending module 20 in an unassembled position but with the first marker 25a on the dilator 26 aligned with the dilator marker, the aperture 12d on the dilator 12. FIG. 3 shows the dilator distal end 26b inserted into the forwardly facing dilator recess 12c in the dilator.

Generally the respective markers are placed at what is referred to as a 12 o'clock position. The 12 o'clock position is defined by the rotational placement position of the side arm stent graft into the vasculature as the anterior position of the vasculature. By such a definition each of the indwelling guide wires can be defined as a clock position from the 12 o'clock position.

FIG. 4 shows in longitudinal cross sectional view the connection arrangement between the nose cone dilator 12 and the length extending module 20. As can be seen in detail in FIG. 4 the length extending module 20 comprises the outer sheath 24 and the extension dilator 26. The extension dilator has a plurality of longitudinal groves 28 on its outside surface. The grooves are generally placed at the 12 o'clock, 3 o'clock, 6 o'clock and 9 o'clock positions. Into these grooves 28 lie the indwelling guide wires 50. The indwelling guide wires 50 are retained in the grooves by the sheath 24. As discussed above the indwelling guide wire crosses over between adjacent longitudinal grooves at 50a. The elongate extension piece 20 also has a guide wire lumen 30.

The longitudinal grooves 28 terminate at 28a before the distal end 26b of the dilator 26. The distal end 26b of the extension dilator 26 fits into the proximal recess 12c in the nose cone dilator 12. As discussed above an aperture 12d extends through the nose cone dilator 12 and opens into proximal recess 12c in the nose cone dilator 12. A trigger wire 29 which extends from the handle of the delivery device enters the hole 12d and then extends into the longitudinal groove 28 just proximal of the end 28a of the groove 28. Hence the distal end 26b of the extension dilator 26 fits into and is retained in proximal recess 12b in the nose cone dilator 12 by a combination of factors. First the terminating recesses 28a means that if the dilator 26 is pulled the trigger wire 29 in the grooves 28 interferes and prevents the removal. Second, the indwelling guide wires can be locked at the handle portion and with the bend at 50a the length extending module cannot move forward and thereby holds the distal end 26b of the dilator 26 in the recess 12c.

Figure 6:
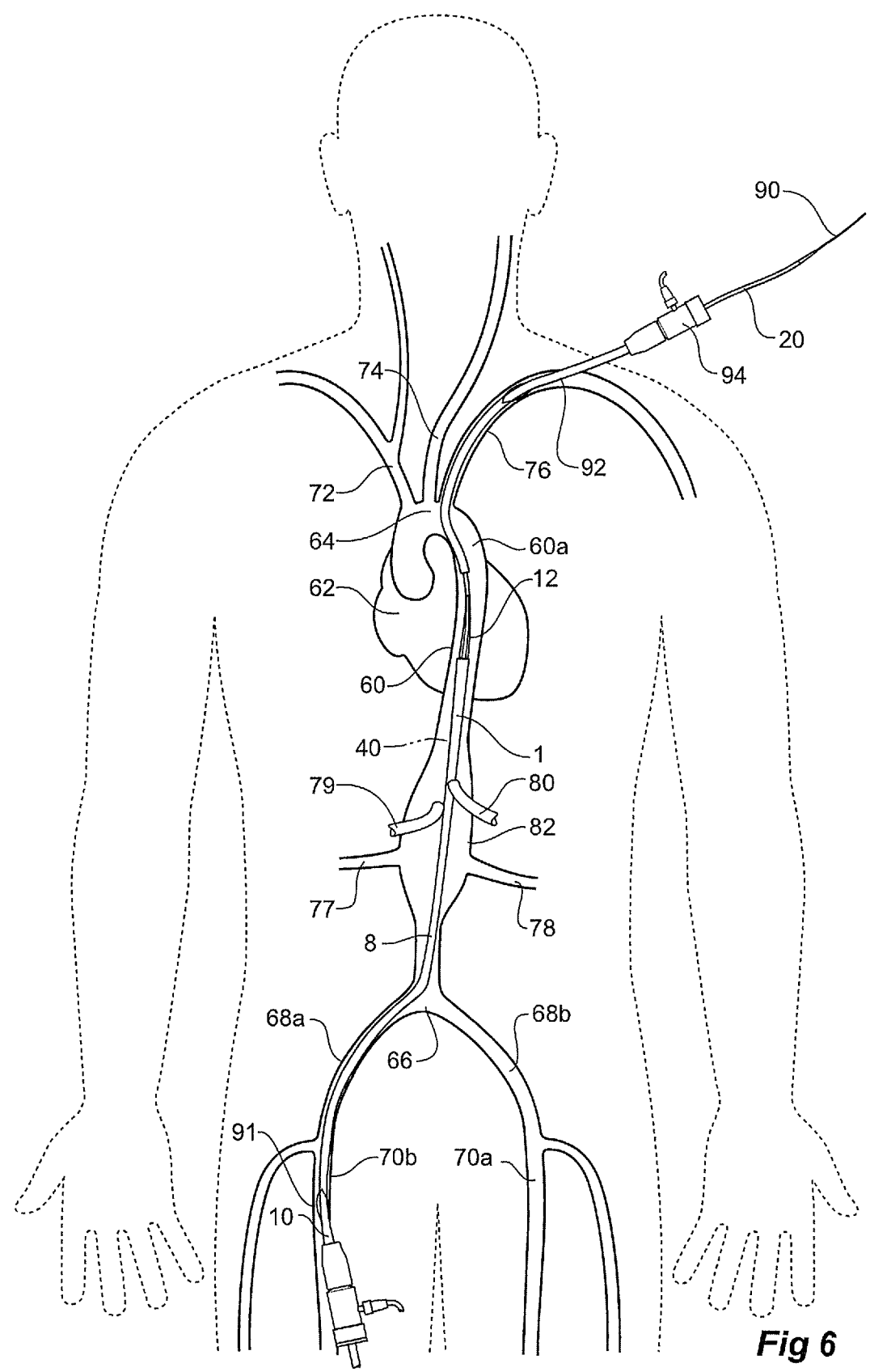
FIG. 6 shows a stage in the deployment of a stent graft using a delivery device according to the present invention.

FIG. 6 shows a schematic view of the vasculature of a human body. The vasculature shown comprises an aorta 60 extending from a heart 62 over a thoracic arch 64 to an aortic bifurcation 66. At the aortic bifurcation, iliac arteries 68a and 68b extend down to respective femoral arteries 70a and 70b. From the thoracic arch the brachiocephalic artery 72, the carotid artery 74 and the left subclavian artery 76 extend.

In the aorta, there are renal arteries 77 and 78 extending from the aorta and little above them the superior mesenteric artery 79 and celiac artery 80. These four arteries can generally be referred to as the pararenal arteries. The aorta 60 is depicted with an aneurism 82 which has occurred in the region of the pararenal arteries and it is desired to deploy a stent graft into the aorta to span the aneurism while at the same time allowing catheterisation and side arm deployment into the renal arteries, the superior mesenteric artery and the celiac artery.

In the first stage of the process of delivery of a side arm stent graft a guide wire is introduced through a femoral puncture 91 into the femoral artery 70a and extended up through the femoral artery 70a, the iliac artery 68b and into the aorta 60 until it is just proximal of the pararenal arteries. A 12 French sheath 92 with sheath hub 94 is introduced via a brachial puncture in the left subclavian artery 76 and the sheath 92 extended down through the left subclavian artery into the descending aorta 60a. A grasper device with a snare is introduced through the sheath hub 94 and down the sheath 92 until the snare can engage the guide wire.

In the next stage the snare is used to draw the guide wire back through the sheath 92 so that it extends out of the hub 94. This establishes a femoral to subclavian through and through wire. A catheter, with or without a dilator, is then introduced through the hub 94 and tracked over the through and through guide wire 90 until it exits the femoral puncture 91. The dilator is then removed leaving the catheter in place.

The proximal end of the extension dilator 26 of the deployment device 1 according to the present invention is introduced into the femoral artery 70b over the guide wire and engaged with the catheter. This assembly is then deployed through the femoral puncture 91. The catheter and the elongate extension 20 of the introduction device 1 track over the guide wire. This is continued until the catheter is completely withdrawn and the extension catheter 24 and extension dilator extend into the sheath 92 and out through the hub 94. At this stage as is shown in FIG. 6, the nose cone dilator 12 of the introduction device is in such a position in the aorta 60 that the stent graft retained within the sheath 8 is in proximity to its desired final position and the length extending module extends out of the shoulder of the patient.

In the next stage the indwelling guide wires 50 are released from the handle portion of the delivery device 1 so that indwelling guide wires 50 can be separated from the elongate extension piece 20 and cut to give four separate indwelling guide wires. The elongate extension piece 20 can then be removed from its selective engagement with the proximal end 12a of the nose cone dilator 12. The indwelling guide wires 50 are then essentially through-and-through guide wires along with the main guide wire 90 but the indwelling guide wires are acting as pre-catheterised guide wires for the various side arms of the stent graft. The guide wires 50 can be recognised to relate a guide wire to a particular side arm of the stent graft by it position in the grooves of the length extending module relative to the second marker 25b (see FIG. 2) as discussed above.

In the next stage the sheath hub 10 is retracted to withdraw the sheath 8 from the stent graft so that the stent graft is at least partially exposed but the proximal end is still retained by means not shown just distal of the nose cone dilator 12.

Figure 7:
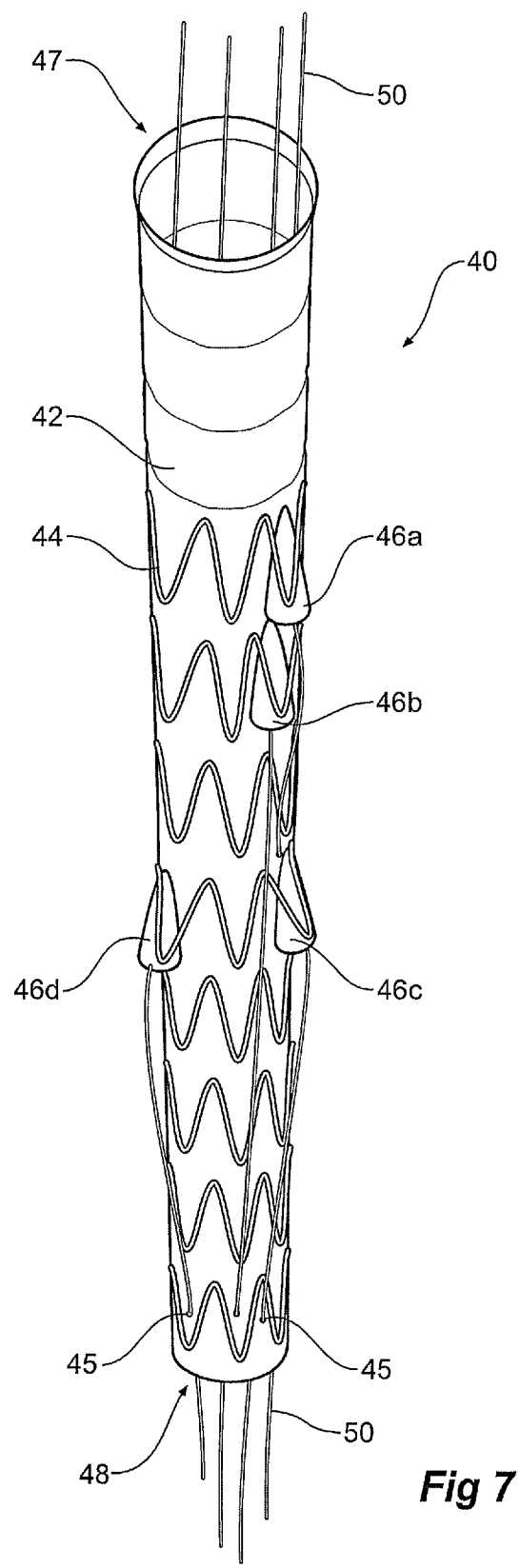
FIG. 7 shows a stent graft with pre-loaded guide wires suitable for the present invention.

A 7 French vessel access sheath and dilator can then be advanced over one of the indwelling guide wires 50 into the hub 94 and through the sheath 92 to exit from the distal end of the sheath 92 and to extend into the interior of the stent graft and out through the distal opening of one of the low profile side arms 46a (see FIG. 7).

At this stage, the Indwelling guide wire 50 still extends through the material of the stent graft distal of the low profile side arm. The dilator of the vessel access sheath can then be retracted from the brachial end of the arrangement and a further guide wire introduced to catheterise the celiac artery 80 (for instance). The indwelling guide wire 50 which still extends through the material of the stent graft distal of the low profile side arm assists in stabilising the vessel access sheath where it extends from the low profile side arm.

Standard catheter and wire techniques can then be used to manipulate the catheter and stiff wire into the selected target vessel to deploy side arms and/or covered bridging stents into each of the pararenal vessels.

As each side arm is deployed the respective indwelling guide wire 50 can be removed.

The sheath 8 can then be retracted to release the distal end of the stent graft and the proximal retention mechanisms can be activated to release the proximal end to fully deploy the stent graft. The introduction device 1 can then be retracted through the femoral puncture 91 and the access sheath 92 retracted through the brachial puncture 93.

Australian Patent No 2010201069 entitled INTRODUCER WITH EXTENSION and PCT Application PCT/US2011/029037 (WO 2011/116308) teach methods for deployment of stent graft using delivery devices incorporating a length extending module and the teachings therein are incorporated herein in their entirety.

FIG. 7 shows a stent graft suitable for use with the present invention. The stent graft as shown in FIG. 7 has a tubular body of a biocompatible graft material which is supported by self expanding zig zag stents. The stent graft has a number of low profile side arms each of which open outside the stent graft facing distally. These side arms are for receiving side arm extensions to extend to the side branch arteries in the region of the renal arteries. The side branch arteries in the region of the renal arteries are the left and right arteries and the superior mesenteric and the celiac arteries. As an alternative to low profile side arms there may be fenestrations or other forms of aperture in the sent graft wall.

The stent graft 40 has a tubular body 42 of a biocompatible graft material which is supported by self expanding zig zag stents 44. The stent graft 40 has a number of low profile side arms 46a, 46b, 46c and 46d each of which open outside the stent graft facing distally. Four indwelling guide wires 50 extend through the stent graft from a proximal end 47 and out through the low profile side arms 46a, 46b, 46c and 46d respectively and extend outside of the stent graft distally of the respective low profile side arms 46a, 46b, 46c and 46d. At a short distance before the distal end 48 of the stent graft the indwelling guide wires 50 extend into the interior of the stent graft through the biocompatible material wall at 45 and continue on distally. Passing the indwelling guide wires 50 back into the material of the stent graft distally of the respective low profile side arms assists in stabilising the guide wire and side arm and assists catheterisation of the branch vessels from the side arms. As can be seen in FIG. 1 the indwelling guide wires 50 extend into the lumen 49 of the pusher catheter 6 and exit at the distal end of the handle 5.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. An endovascular stent graft delivery device comprising an elongate body and a length extending module:
   the elongate body comprising a distal portion to remain outside a patient in use and a proximal portion to be introduced into the body to carry a stent graft to a placement site, the proximal portion comprising a nose cone dilator at the proximal end thereof,
   the length extending module extending proximally of the nose cone dilator, the length extending module comprising a distal end releasably fastened to the nose cone dilator and a proximal end,
   the length extending module comprising a plurality of longitudinal grooves, each having a distal terminus and a proximal terminus at the distal end and the proximal end of the length extending module, respectively,
   the nose cone dilator comprising a dilator marker and the length extending module comprising a first marker and a second marker, the first marker being at the distal end of the length extending module and longitudinally spaced apart from the distal terminus of the longitudinal grooves, the second marker being at the proximal end of the length extending module and longitudinally spaced apart from the proximal terminus of the longitudinal grooves, the first marker and the second marker being at the same relative circumferential position on the length extending module and the length extending module being releasably fastened to the nose cone dilator with the first marker and the dilator marker rotationally aligned, whereby the rotational position of the of the portion of the length extending module having the second marker within the patient can be determined by the observation of the position of the second marker relative to the first marker.

2. The endovascular stent graft delivery device as in claim 1 wherein the dilator marker comprises an aperture in the nose cone dilator.

3. The endovascular stent graft delivery device as in claim 1 wherein the first marker and the second marker each comprises a recess in the length extending module.

4. The endovascular stent graft delivery device as in claim 1 comprising a plurality of indwelling guide wires extending from the distal portion of the elongate body to the nose cone dilator and through the length extending module, whereby the endovascular stent graft delivery device can be introduced into a patient via a femoral artery and the length extending module can extend out an artery of the thoracic arch whereby to extend the indwelling guide wires out of the artery of the thoracic arch.

5. A stent graft delivery device as in claim 4 wherein the nose cone dilator at the proximal end of the elongate body comprises a plurality of longitudinal grooves on an outside surface thereof to receive respective indwelling guide wires therealong.

6. A stent graft delivery device as in claim 5 wherein the plurality of longitudinal grooves on at least part of the outside surface of the nose cone dilator comprise a substantially closed tube except for a narrow elongated opening whereby the respective indwelling guide wires are received and retained therein.

7. A stent graft delivery device as in claim 1 wherein the length extending module comprises an elongate extension sheath and an extension dilator in the extension sheath and the extension dilator extending distally and proximally of the extension sheath, the extension dilator comprising an outside surface, the plurality of longitudinal grooves on the outside surface, and a plurality of indwelling guide wires extending along respective longitudinal grooves.

8. A stent graft delivery device as in claim 7 wherein a stent graft is carried on the proximal portion of the elongate body, the stent graft comprising a tubular body, the tubular body comprising proximal and distal open ends and a plurality of fenestrations or side arms, each of the indwelling guide wires extending through a respective fenestration or side arm, the indwelling guide wires extending through the tubular body proximally of the respective fenestration or side arm and outside the tubular body distally of the respective fenestration or side arm.

9. A stent graft delivery device as in claim 1 wherein the nose cone dilator comprises a proximal aperture and the length extending module is removably engaged into the proximal aperture.

10. A stent graft delivery device as in claim 1 wherein the length extending module is removably engaged with the nose cone dilator by a trigger wire release mechanism, whereby upon release of the trigger wire release mechanism the length extending module can be removed from the nose cone dilator.

11. A stent graft delivery device as in claim 10 wherein the length extending module comprises a pair of cross apertures extending into the extension dilator between adjacent longitudinal grooves at the proximal end of the extension dilator whereby each of a first and second indwelling guide wires passes through a respective cross aperture to return in an adjacent longitudinal groove.

12. A stent graft delivery device as in claim 4 wherein the plurality of indwelling guide wires comprise a first and a second continuous indwelling guide wire, each continuous wire extending from the distal portion to the proximal end of the length extending module and returning to the distal portion.

13. A stent graft delivery device as in claim 1 wherein the first marker, the second marker and the dilator marker are configured to be placed at a 12 o'clock position with respect to the vasculature of a patient, the 12 o'clock position being the anterior position of the vasculature.

14. A length extending module for an endovascular delivery device, the length extending module being able to be releasably fastened to a dilator of the endovascular delivery device and arranged to extend proximally of the dilator in use, the length extending module comprising a distal end which is able to be releasably fastened to the dilator and received into a proximal aperture, the length extending module comprising a proximal end which in use extends out of a patient, the length extending module comprising an extension dilator, the extension dilator comprising at least one longitudinal groove, each having a distal terminus and a proximal terminus at a distal end and a proximal end of the extension dilator, respectively, the length extending module comprising a first marker and a second marker, the first marker located on the distal end of the extension dilator and longitudinally spaced apart from the distal terminus of the longitudinal grooves, the second marker located on the proximal end of the extension dilator and longitudinally spaced apart from the proximal terminus of the longitudinal grooves, the first marker and the second marker being at the same relative circumferential position whereby the rotational position of the portion of the length extending module having the second marker of the endovascular delivery device within the patient can be determined by the observation of the position of the second marker relative to the first marker.

15. The length extending module as in claim 14 wherein the first marker and the second marker each comprises a recess in the extension dilator.

16. The length extending module as in claim 14 wherein the length extending module comprises an elongate extension sheath, the extension dilator is disposed within the extension sheath and extends distally and proximally along the extension sheath, the extension dilator comprising an outside surface, the at least one longitudinal groove on the outside surface.

17. The length extending module as in claim 14 wherein the length extending module comprises a pair of cross apertures extending into the extension dilator between adjacent longitudinal grooves at the proximal end of the extension dilator whereby in use a plurality of indwelling guide wires cross through a respective cross aperture to return in an adjacent longitudinal groove.

18. An endovascular stent graft delivery device comprising:
an elongate body and a length extending module;
the elongate body comprising a distal portion to remain outside a patient in use and a proximal portion to be introduced into the body to carry a stent graft to a placement site, the proximal portion comprising a nose cone dilator at the proximal end thereof;
the nose cone dilator comprising a plurality of longitudinal grooves on an outside surface thereof to receive respective indwelling guide wires therealong;
the length extending module comprising an extension sheath and an extension dilator in the extension sheath;
the extension dilator extending proximally of the nose cone dilator, the extension dilator comprising a distal end being releasably fastened to the nose cone dilator and received into a proximal aperture, the extension dilator comprising a proximal end, the nose cone dilator comprising a dilator marker and the extension dilator comprising a first marker and a second marker, the extension dilator comprising a plurality of longitudinal grooves, each having a distal terminus and a proximal terminus at the distal and the proximal ends of the extension dilator, respectively; and
the first marker being at the distal end of the extension dilator and longitudinally spaced apart from the distal terminus longitudinal grooves and located inside the proximal aperture, the second marker being at the proximal end of the extension dilator and longitudinally spaced apart from the proximal terminus of the longitudinal grooves, the first marker and the second marker being at the same relative circumferential position on the extension dilator, the extension dilator releasably fastened to the nose cone dilator with the first marker and the dilator marker rotationally aligned whereby the rotational position of one part of the elongate body within the patient relative to another part of the elongate body can be determined by the observation of the position of the second marker relative to the first marker.

19. A stent graft delivery device as in claim 18 wherein the dilator marker comprises an aperture that extends through the nose cone dilator.

20. A stent graft delivery device as in claim 19 wherein the first marker and the second marker each comprises a recess on the extension dilator.

\* \* \* \* \*